US011116518B2

(12) United States Patent
Hafez et al.

(10) Patent No.: US 11,116,518 B2
(45) Date of Patent: Sep. 14, 2021

(54) THREE-IN-ONE PATIENT-SPECIFIC TEMPLATE FOR USAGE IN ANKLE REPLACEMENTS SURGERIES

(71) Applicant: Mahmoud Alm El Din Hafez, Giza (EG)

(72) Inventors: Mahmoud Alm El Din Hafez, Giza (EG); Ahmed Abdel Moghny Salem, Giza (EG)

(73) Assignee: Mahmoud Alm El Din Hafez, Giza (EG)

( * ) Notice: Subject to any disclaimer, the term of this patent is extended or adjusted under 35 U.S.C. 154(b) by 0 days.

(21) Appl. No.: 16/763,691

(22) PCT Filed: Nov. 8, 2018

(86) PCT No.: PCT/EG2018/000028
§ 371 (c)(1),
(2) Date: May 13, 2020

(87) PCT Pub. No.: WO2019/091537
PCT Pub. Date: May 16, 2019

(65) Prior Publication Data
US 2020/0367910 A1    Nov. 26, 2020

(30) Foreign Application Priority Data

Nov. 13, 2017 (EG) .................... 2017110029
May 13, 2018 (EG) .................... 2018050805

(51) Int. Cl.
*A61B 17/58* (2006.01)
*A61B 17/60* (2006.01)
(Continued)

(52) U.S. Cl.
CPC .......... *A61B 17/15* (2013.01); *A61B 17/1775* (2016.11); *A61B 17/56* (2013.01); *A61B 90/39* (2016.02); *A61B 2017/568* (2013.01)

(58) Field of Classification Search
CPC combination set(s) only.
See application file for complete search history.

(56) References Cited

U.S. PATENT DOCUMENTS

2016/0361071 A1   12/2016  Mahfouz
2017/0296208 A1*  10/2017  Lian .................... A61B 17/1775

FOREIGN PATENT DOCUMENTS

WO    2014020562 A1    2/2014
WO    2016148675 A1    9/2016

* cited by examiner

*Primary Examiner* — Sameh R Boles
(74) *Attorney, Agent, or Firm* — Dickinson Wright PLLC; Andrew D. Dorisio

(57) ABSTRACT

This invention relates to a custom made cutting block for total ankle replacement consisting of two pieces, one for tibia and other for talus. The block can be using in 3 ways as pin locator, cutting block or in coupling with the other conventional instruments. The block provides a unique method for matching with the tibia and talus based on the CT-scan imaging The block allows the surgeons to detect the correct position of the tibia pin guide and talus pin guide in addition with the volume of bone cutting in tibia to perform the total ankle replacement surgery. The block provides the surgeon by the size of implant and optimum length of the screws. The block can coupling with the other conventional tool in easy plugging method with give a wide range of varieties to the surgeon to preform and detect a correct position of the prosthesis in total ankle arthroplasty.

9 Claims, 5 Drawing Sheets

(51) Int. Cl.
*A61F 2/00* (2006.01)
*A61B 17/15* (2006.01)
*A61B 17/17* (2006.01)
*A61B 17/56* (2006.01)
*A61B 90/00* (2016.01)

THREE-IN-ONE PATIENT-SPECIFIC TEMPLATE FOR USAGE IN ANKLE REPLACEMENTS SURGERIES

This application claims the benefit of Egyptian Provisional application No. 29/2017 filed on Nov. 13, 2017 and Egyptian Patent Application No. 805/2018 on May 13, 2018

TECHNICAL FIELD

The present invention is related to a three-in-one patient-specific template for usage in ankle replacement surgeries.

PRIOR ART

Ankle replacement surgery is a complicated procedure and should only be performed by a competent orthopedic surgeon. The best mode to carry out this surgery is to use the techniques of patient-specific electronic templates. The currently available templates are the electronic ones, which are used as a spatial guide only for determining the location, alignment and placement of the conventional surgical cutting tools, but may not be used for making the necessary surgical cuts as required for implanting an ankle prosthetic joint. In addition, they cannot be used as an auxiliary guide for determining the location, alignment and placement of the conventional surgical cutting tools. A second type is used as a spatial guide and may be used for making the necessary surgical cuts as required for implanting an ankle prosthetic joint. This latter type comprises two separate pieces, one for making the necessary tibial cuts and the other for making the necessary talar cuts.

DEFICIENCIES IN PRIOR ART

The currently available templates are the electronic ones, which are used as a spatial guide only for determining the location, alignment and placement of the conventional surgical cutting tools, but may not be used for making the necessary surgical cuts as required for implanting an ankle prosthetic joint. In addition, they cannot be used as an auxiliary guide for determining the location, alignment and placement of the conventional surgical cutting tools. The second type of prior art templates is used as a spatial guide and may be used for making the necessary surgical cuts as required for implanting an ankle prosthetic joint. However, it comprises two separate pieces, one for making the necessary tibial cuts and the other for making the necessary talar cuts.

In both types, perpendicular openings are used for fixing the template on the bone surface, thereby not providing the surgeon with a substantial insight for ensuring the complete fixation of the template on the tibia and talus. In addition, the second type used as a surgical guide for the necessary cuts must be accompanied by external aid tools, such as fixation tools and tools for ensuring that the leg and foot are mutually perpendicular during the surgery. Proper alignment is a critical step in ankle replacement surgeries. However, prior art templates do not address this problem, thereby necessitating the usage of other surgical aid tools to complete the surgical operation.

The design of prior art templates does not enable the attachment between the electronic template and the conventional surgical tools. This deficiency restricts surgeons to the only available sizes of prosthetic joints and makes them unable to modify the secondary cutting procedures in the tibia and talus in case the desired size is not available during the surgery.

In view of the said challenges in prior art, there is still a need for a novel invention that may overcome these problems and provide new alternatives for surgeons that would make ankle replacement surgeries less complicated and increase their success rates.

DISCLOSURE OF THE INVENTION

Provided is a patient-specific template for usage in ankle replacement surgeries. The template, according to the present invention, comprises one piece with paths therein to make the main cuts in the tibial section of the joint, a socket fixed on the talar section of the template to make a cavity for the talar section of the joint, and four openings, two of which are parallel while the others are arranged obliquely to ensure the correct fixation of the template on the tibia and talus. The template further comprises other four openings, two of which are in the tibial section and the others are in the talar section for usage as a spatial guide for the location, alignment and placement of the conventional cutting tools. Openings arranged in the tibial and talar sections of the template serve as reference points to make the required attachment between the template and the conventional surgical tools to complete bone fixation and cuts.

DETAILED DESCRIPTION OF THE INVENTION

The present invention is related to a patient-specific template for usage in ankle replacement surgeries by the help of preoperative planning. A process for producing a patient-specific template is also provided. The template, according to the present invention, may be used according to the physician's discretion and the patient's medical condition.

The patient-specific template, according to the present invention, comprises one piece with cut paths and fixation openings therein. The said template may be used in one of three ways, subject to the physician's discretion, the patient's medical condition, the facilities of the operating room, and the availability of the dimensions and shapes of the prosthetic joint. The three ways are: a surgical guide for making the necessary cuts in the tibia and talus, a spatial guide for determining the location, alignment and placement of the conventional surgical cutting tools, or a preliminary template for being attached to the conventional surgical tools according to the physician's discretion (see FIGS. 1 and 2).

The template, according to the present invention, comprises one piece with paths therein to make the main cuts in the tibial section of the joint, a socket fixed on the talar section of the template to make a cavity for the talar section of the joint, and four openings, two of which are parallel while the others are arranged obliquely to ensure the correct fixation of the template on the tibia and talus. The template further comprises other four openings, two of which are in the tibial section and the others are in the talar section for usage as a spatial guide for the location, alignment and placement of the conventional cutting tools commonly used for making the necessary tibial and talar cuts. Openings arranged in the tibial and talar sections of the template serve as reference points to make the required attachment between the template and the conventional surgical tools to complete bone fixation and cuts (see FIGS. 1 and 2).

Software-assisted preoperative planning includes taking a two-dimensional CT scan for the patient, which is then converted into a 3D model for the bones of the ankle joint with its two sections, the tibia and the talus. Preoperative planning is done on a specialized computer program to determine the location, alignment and dimensions of the ankle prosthetic joint. The CT scan matches the profile of the patient's bones, thereby enabling the design of a patient-specific electronic template for usage in ankle replacement surgeries.

Preoperative planning depends on the mechanical axis of the tibia to enable the surgeon to determine the location, alignment and placement of the tibial section of the ankle joint and also the quantity of bones to be cut, whether from the tibial section or the talar section (see FIG. 3).

The design of the electronic template with its tibial and talar sections depends on the sizes and dimensions of the prosthetic joints as produced by manufacturing companies. This allows the surgeon to select the appropriate size and profile of the prosthesis during the preoperative planning step.

As outlined above, the template, according to the present invention, comprises one piece and performs three functions: a cut guide, a spatial guide and a preliminary template for attachment with the conventional surgical tools.

In case of being used as a surgical cut guide, the template, according to the present invention, comprises paths to make three main cuts (i.e. horizontal, vertical and oblique) in the tibial section of the ankle joint. It further comprises a socket fixed on the talar section of the template to make a cavity for the talar section of the joint. The paths are used by the surgeon to make the necessary surgical cuts as preplanned on the computer program (see FIGS. 1 and 2).

In case of being used as a spatial guide, the template, according to the present invention, comprises four openings, two of which are in the tibial section and the others are in the talar section, for determining the location, alignment and placement of the conventional cutting tools commonly used for making the necessary tibial and talar cuts. An equal distance separates every two openings, whether those in the tibial section or those in the talar section. The said distance matches the distance separating between the openings in a typical cutting template. In addition, the two openings in the electronic template are parallel to each other. The surgeon may use the said openings for inserting a long surgical wire in the tibia or talus, then removing the template, while keeping the surgical wire in place inside the bone, to use it as a guide for inserting the conventional cutting template in the same place and finally implanting an ankle prosthetic joint. Hence, in this case, the electronic template serves as a spatial guide for the conventional cutting tools. The exact position of the template on the tibia and talus is determined according to the mechanical axis of the tibia to determine the location, alignment and placement of the prosthetic joint to be implanted (see FIGS. 1 and 2).

In case the template, according to the present invention, is used as a preliminary template for attachment to the conventional tools, it comprises four openings on the tibial and talar sections thereof to serve as reference points for making the required attachment between the template and the conventional surgical tools used for making the necessary bone fixation and cuts. In this case, the location of the template on the tibia and talus is first determined then the template is attached to the conventional cutting templates through the four openings comprised thereon, which are identical to those comprised on the conventional cutting templates (see FIGS. 1 and 2).

The template is fixed on the tibia and talus by means of four openings, two of which are parallel and the other two are arranged obliquely to ensure the correct fixation of the template on the tibia and foot bone. The internal surface of the template includes features typically matching those on the bone surface in the exact location where the template is to be arranged, as outlined in the software-assisted preoperative planning and the patient's CT scan. The two oblique openings on the tibia and the exact match between the internal surface features of the template and the bone surface features ensure zero movement of the template. This allows the surgeon to arrange the template on the bone in just one location, since this patient-specific template matches the anatomic profile of the respective bone as shown in the CT scan (see FIGS. 4 and 5).

The CT scan made to the patient gives an explicit image of the condition of only the bones, without revealing the cartilage or soft tissues. Data derived from this CT scan is inputted into a computer program. Another advantage of the template, according to the present invention, is its production depending on the patient's CT scan, which does not change over time unlike the MRI scan which may change with the change in the cartilage condition and its erosion percentage. The said CT scan is converted into a 3D model for the tibia and talus. Afterwards, operative planning is made as outlined above depending on the mechanical axis and the anatomic features of the ankle joint.

At this point, the computer program begins producing an electronic form for the template, according to the size, placement and alignment of the prosthetic joint as preplanned by the computer program. The internal surface of the template shall well match the profile of the bone external surface to ensure the best fitting of the template thereon.

The template electronic form is sent to a 3D printer to produce a real model that may be used in surgical operations. The template contains printed data about the size and direction of the joint (whether it is the right or left joint), and the name of the patient to prevent any confusion or loss between templates.

The template, according to the present invention, may be easily sterilized. In addition, it is easy to carry because of its light weight and small size. The weight of the template is 200 g at most, unlike the conventional tools whose weight exceeds 50 kg. Moreover, the said conventional tools are composed of many parts, thereby requiring longer sterilization time, and they are difficult to move from one place to another.

INDUSTRIAL APPLICABILITY

The patient-specific template may be used in ankle replacement surgeries. It comprises one piece with cut paths and fixation openings therein. It may be used in one of three ways, subject to the physician's discretion, the patient's medical condition, the facilities of the operating room, and the availability of the dimensions and shapes of the prosthetic joint. The three ways are: a surgical guide for making the necessary cuts in the tibia and talus, a spatial guide for determining the location, alignment and placement of the conventional surgical cutting tools, or a preliminary template for being attached to the conventional surgical tools according to the physician's discretion Three-dimensional printers are used for producing the said template. The template may be used only once for one patient because its design is based on the patient's CT scan, which cannot be similar to that of any other individual.

The template, according to the present invention, may be used by surgeons for implanting ankle prosthetic joints by means of software-assisted preoperative planning.

DESCRIPTION OF THE FIGURES

FIG. (1) is a two-dimensional front elevation for a three-in-one patient-specific template for usage in ankle replacement surgeries, illustrating paths thereof for making internal cuts in the tibial section of the joint (i.e. horizontal (1), vertical (2) and oblique (3) cuts, respectively). The figure also shows the horizontal fixation openings (5, 7), the oblique fixation openings (6), the socket (4) for making a cavity for arranging the talar section of the joint, and the openings (7) for making the required attachment to the conventional surgical tools.

FIG. (2) is a three-dimensional view for the three-in-one patient-specific template for usage in ankle replacement surgeries, illustrating paths thereof for making internal cuts in the tibial section of the joint (i.e. horizontal (1), vertical (2) and oblique (3) cuts, respectively). The figure also shows the horizontal fixation openings (5, 7), the oblique fixation openings (6), the socket (4) for making a cavity for arranging the talar section of the joint, and the openings (7) for making the required attachment to the conventional surgical tools.

Figure 1:
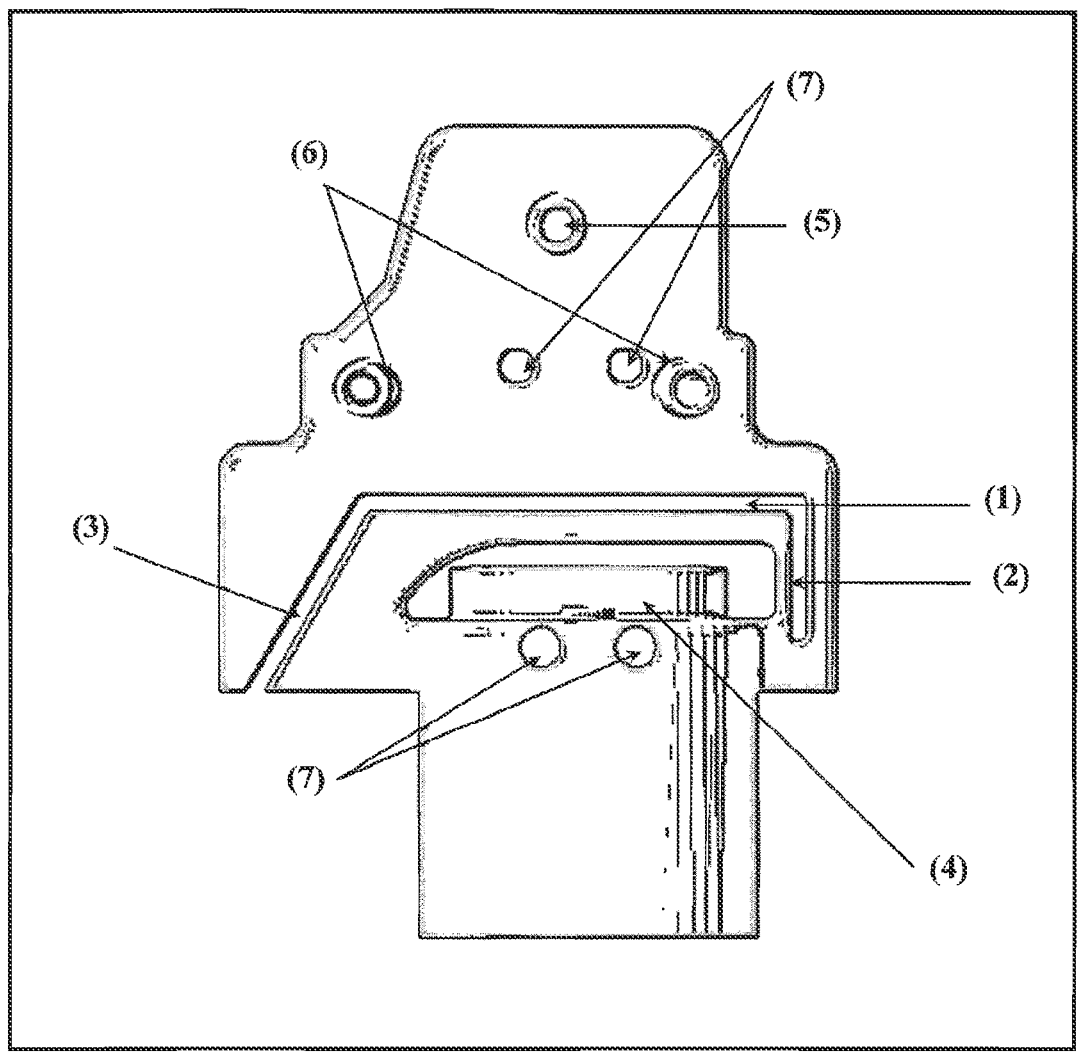
Figure 2:
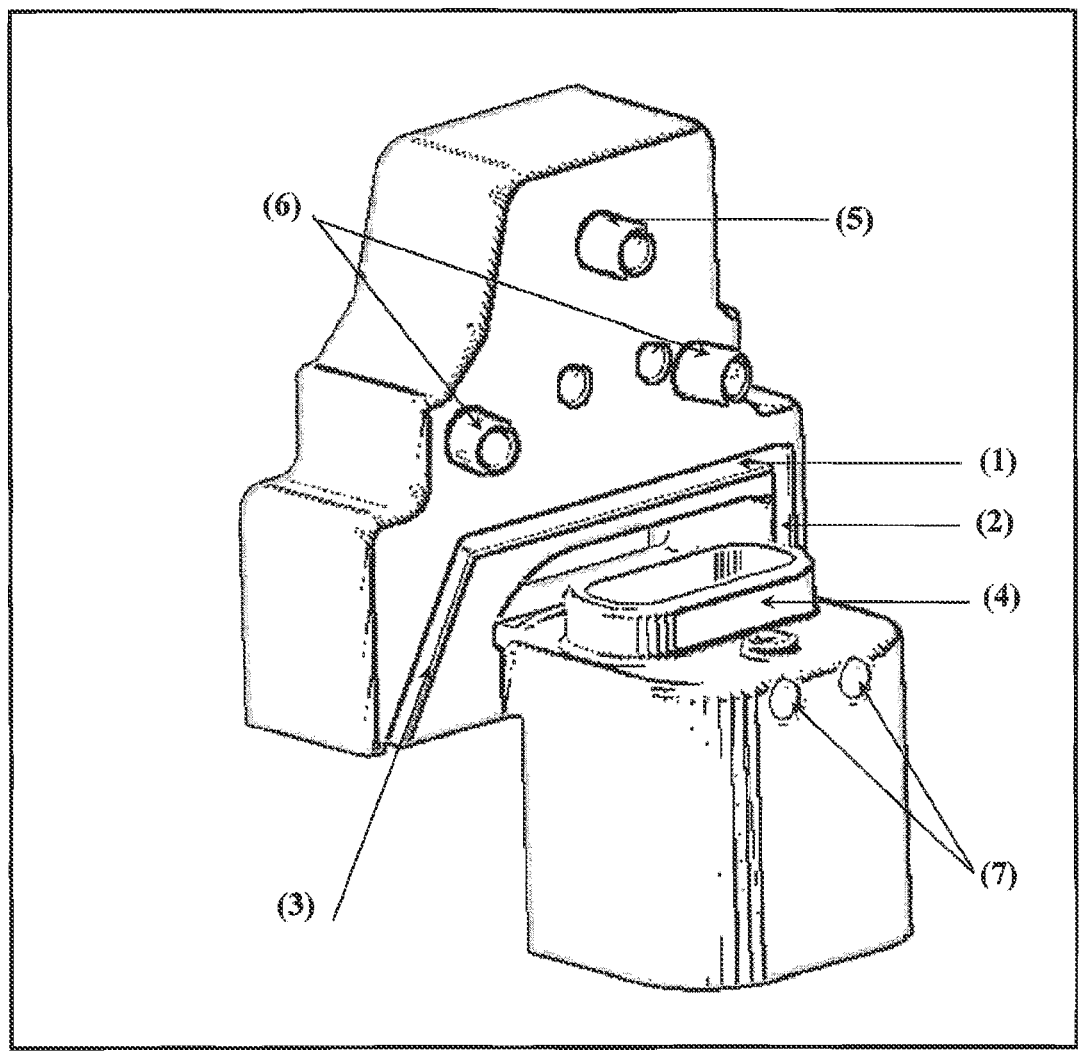
Figure 3:
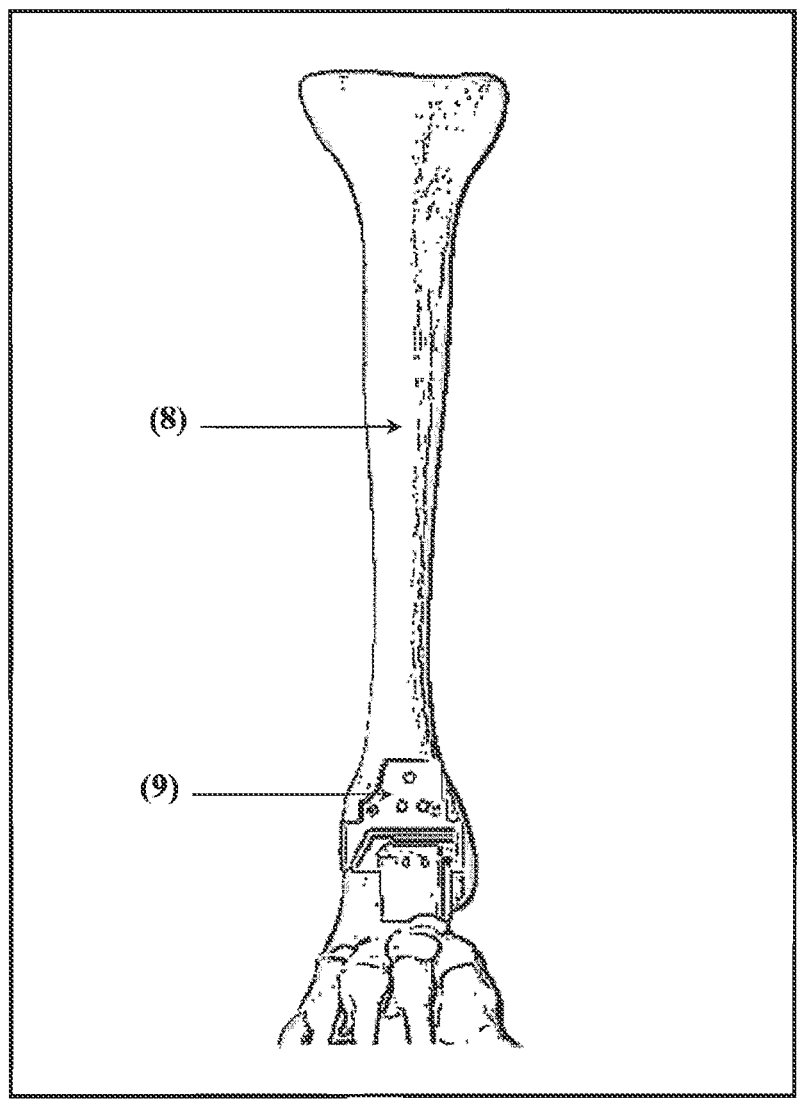
Figure 4:
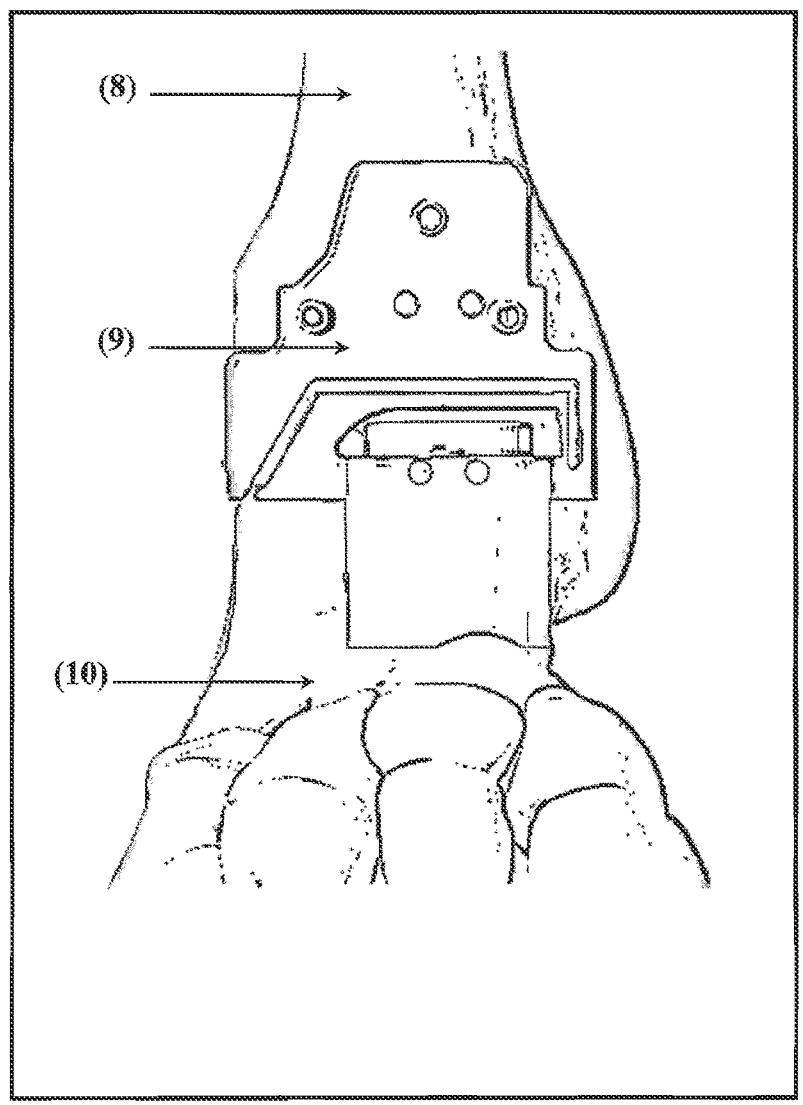
Figure 5:
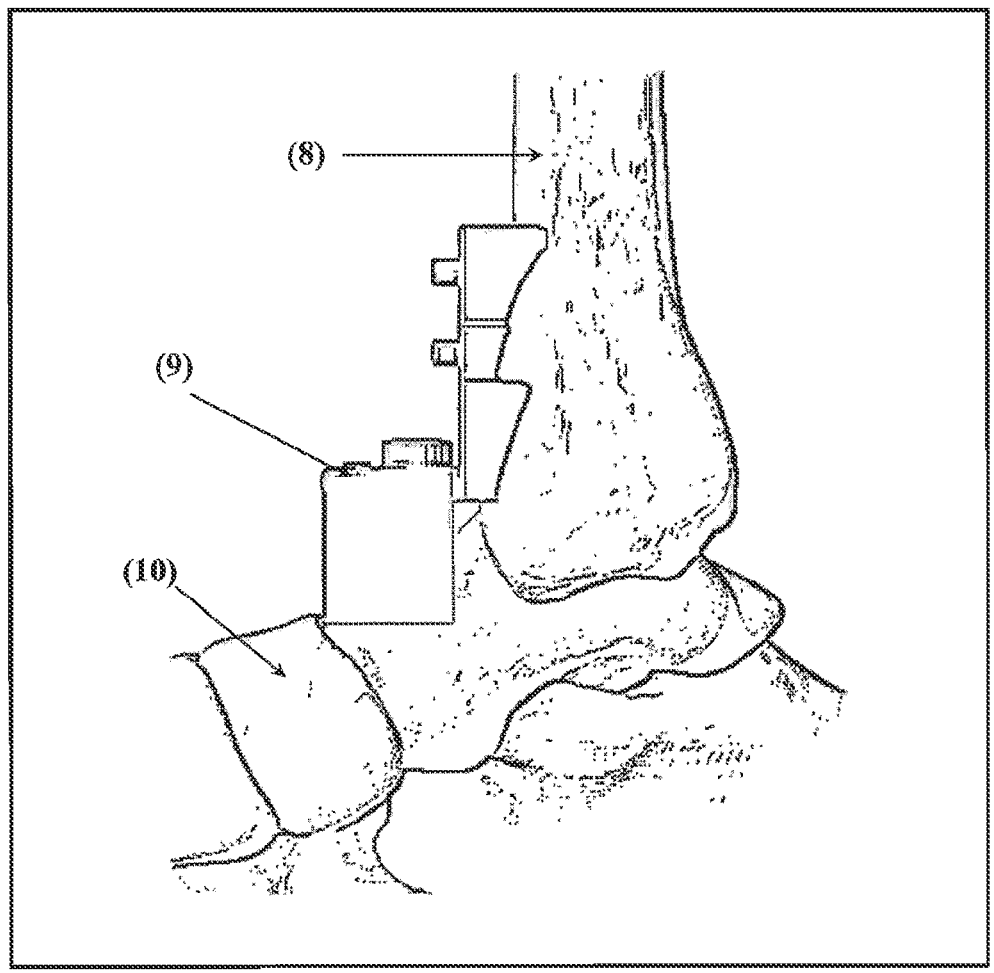

FIG. (3) is a two-dimensional front elevation for the three-in-one patient-specific template for usage in ankle replacement surgeries with the ankle prosthetic joint (9) placed on the tibia and talus to show its alignment to the mechanical axis of the tibia (8).

FIG. (4) is a two-dimensional front elevation for the three-in-one patient-specific template for usage in ankle replacement surgeries with the ankle prosthetic joint (9) placed on the tibia (8) and talus (10) in the exact right location as determined by the preoperative planning.

FIG. (5) is a two-dimensional side elevation for the three-in-one patient-specific template for usage in ankle replacement surgeries with the ankle prosthetic joint (9) placed on the tibia (8) and talus (10) in the exact right location as determined by the preoperative planning.

The invention claimed is:

1. A patient-specific template for usage in ankle replacement surgeries, comprising one piece with paths therein to make the main cuts in the tibial section of the joint, a socket fixed on the talar section of the template to make a cavity for the talar section of the joint, and four openings, two of which are parallel while the others are arranged obliquely to ensure the correct fixation of the template on the tibia and talus, wherein the said template further comprises other four openings, two of which are in the tibial section and the others are in the talar section for usage as a spatial guide for the location, alignment and placement of the conventional cutting tools commonly used for making the necessary tibial and talar cuts, and wherein openings comprised in the tibial and talar sections of the said template serve as reference points to make the required attachment between the template and the conventional surgical tools to complete bone fixation and cuts.

2. The template, according to claim (1), wherein it comprises one piece having vertical and horizontal sides.

3. The template, according to claim (2), wherein the vertical side thereof comprises three paths to make vertical, horizontal, and oblique cuts in the tibial section of the ankle joint.

4. The template, according to claim (2), wherein the vertical side thereof comprises three openings with different diameters to arrange the template on the tibia, and wherein two of the said openings are arranged obliquely on the tibia while the remaining opening is arranged perpendicularly to the tibia on the middle of the template from the top.

5. The template, according to claim (2), wherein the horizontal side thereof comprises a socket fixed on the talar section of the template to make a cavity for the talar section of the joint, and wherein it further comprises an oblique path for making an oblique cut in the talar section of the joint.

6. The template, according to claim (2), wherein the horizontal side thereof comprises a perpendicular opening to arrange the template on the foot bone.

7. The template, according to claim (1), wherein the one piece thereof comprises four openings, two of which are in the tibial section and the others are in the talar section, for determining the location, alignment and placement of the conventional cutting tools, and wherein an equal distance separates every two openings and matches the distance separating between the openings in a typical cutting template used for making the tibial and talar cuts.

8. The template, according to claim (1), wherein it comprises openings in the tibial and talar sections thereof to serve as reference points to make the required attachment between the template and the conventional surgical tools to complete bone fixation and cuts.

9. The template, according to claim (8), wherein it comprises two openings in the tibial section thereof for making the required attachment between the template and the conventional surgical tools used for making the main cuts in the tibial section of the joint, and wherein it further comprises two openings on the talar section thereof for making the required attachment between the template and the conventional surgical tools used for making the main cuts in the talar section of the joint.

* * * * *